US009427690B2

(12) United States Patent
Jung et al.

(10) Patent No.: US 9,427,690 B2
(45) Date of Patent: Aug. 30, 2016

(54) APPARATUS AND METHOD FOR FABRICATING ANTI-MICROBIAL AIR FILTER MEDIA AND ANTI-MICROBIAL AIR FILTER MEDIA

(71) Applicant: KOREA INSTITUTE OF SCIENCE AND TECHNOLOGY, Seoul (KR)

(72) Inventors: Jae Hee Jung, Cheongju-si (KR); Gwi Nam Bae, Seoul (KR); Bo Mi Kwon, Seoul (KR); Gi Byoung Hwang, Yeongju-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 737 days.

(21) Appl. No.: 13/686,192

(22) Filed: Nov. 27, 2012

(65) Prior Publication Data

US 2013/0291736 A1 Nov. 7, 2013

(30) Foreign Application Priority Data

May 3, 2012 (KR) .................. 10-2012-0046865

(51) Int. Cl.
| | |
|---|---|
| *B01D 46/00* | (2006.01) |
| *B32B 37/14* | (2006.01) |
| *B05C 11/00* | (2006.01) |
| *B05C 11/10* | (2006.01) |
| *A01N 25/00* | (2006.01) |
| *B32B 33/00* | (2006.01) |
| *B32B 37/24* | (2006.01) |

(52) U.S. Cl.
CPC ........... *B01D 46/0028* (2013.01); *A01N 25/00* (2013.01); *B05C 11/1042* (2013.01); *B32B 33/00* (2013.01); *B32B 37/144* (2013.01); *B32B 37/24* (2013.01); *B32B 2307/202* (2013.01); *B32B 2307/7145* (2013.01)

(58) Field of Classification Search
USPC ...................................... 156/313, 379.9, 390
See application file for complete search history.

(56) References Cited

U.S. PATENT DOCUMENTS

| | | | | |
|---|---|---|---|---|
| 2005/0170070 | A1* | 8/2005 | Layrolle | ............. A61F 2/30767 427/2.1 |
| 2013/0161847 | A1* | 6/2013 | Hwang | ................ B29C 35/002 264/6 |

FOREIGN PATENT DOCUMENTS

| | | | | |
|---|---|---|---|---|
| JP | 11-267419 | A | 10/1999 | |
| JP | 2002-001024 | A | 1/2002 | |
| JP | 2003-001028 | A | 1/2003 | |
| KR | 10-1996-0007504 | A | 3/1996 | |
| KR | 20-0365133 | Y1 | 10/2004 | |
| KR | 10-2005-0009974 | A | 1/2005 | |
| KR | 10-2005-0123067 | A | 12/2005 | |
| KR | 10-2006-0129593 | A | 12/2006 | |
| KR | 10-2009-0004611 | A | 1/2009 | |
| KR | 10-2009-0048703 | | * 5/2009 | ............. B01D 39/00 |
| KR | 10-2009-0048703 | A | 5/2009 | |
| KR | 10-2011-0100088 | A | 9/2011 | |
| KR | 10-2011-0111570 | A | 10/2011 | |
| KR | 10-2011-0128464 | | * 11/2011 | ............. B01D 39/00 |
| KR | 10-2011-0128464 | A | 11/2011 | |

* cited by examiner

*Primary Examiner* — Dah-Wei D Yuan
*Assistant Examiner* — Jethro M Pence

(57) ABSTRACT

The present disclosure relates to an antimicrobial filter medium with improved antimicrobial property and microbe capture ability wherein gaseous antimicrobial nanoparticles are uniformly coated onto the filter medium and conductive members are attached on both sides of the filter medium, and an apparatus and a method for fabricating the same.

9 Claims, 5 Drawing Sheets

351 high electric voltage generator
352 Ground

Microbe spray unit → Diffusion drying unit → 310 → Discharge

APPARATUS AND METHOD FOR FABRICATING ANTI-MICROBIAL AIR FILTER MEDIA AND ANTI-MICROBIAL AIR FILTER MEDIA

CROSS-REFERENCE TO RELATED APPLICATION

This application claims priority to Korean Patent Application No. 10-2012-46865, filed on May 3, 2012, and all the benefits accruing therefrom under 35 U.S.C. §119, the contents of which in its entirety are herein incorporated by reference.

BACKGROUND

1. Field

The present disclosure relates to an antimicrobial filter medium and an apparatus and a method for fabricating the same. More specifically, the disclosure relates to an antimicrobial filter medium with improved antimicrobial property and microbe capture ability wherein gaseous antimicrobial nanoparticles are uniformly coated onto the filter medium and conductive members are attached on both sides of the filter medium, and an apparatus and a method for fabricating the same.

2. Description of the Related Art

As concerns over health and environment increase gradually, purification of indoor air directly affecting human health is becoming an important social issue. It is because the time spent indoors is increasing in modern society and thus the effect of indoor environment on our lives is also increasing.

Various airborne microorganisms can be harmful to the human body float in indoor air, including bacteria, fungi and viruses. These microorganisms cause airborne infections and environmental diseases and may negatively affect the human body and environment. Although these airborne microorganisms can be primarily filtered by an air filter used to remove dust, microorganisms of sub-micron sizes such as bacteria and viruses are not filtered by common air filters. To remove bacteria, viruses, etc., a high-performance filter with a very small filter pore size is necessary. But, the increased pressure across the filter may lead to increased load of the air filter system. And, unlike other airborne particles, airborne microorganisms may proliferate on the surface of the filter medium depending on the environmental and nutritional conditions and may be brought indoors again and generate microbial volatile organic compounds (MVOCs) causing offensive odor.

To solve these problems, a method of coating an organic or inorganic antibacterial agent in liquid state on the surface of a filter medium is proposed to suppress the proliferation of microorganisms (Korean Patent Publication No. 2009-4611). However, since most of the existing methods including that of Korean Patent Publication No. 2009-4611 adopt a strategy of coating an antibacterial agent in liquid state on the filter surface, a large amount of the antibacterial agent is necessary and the method is inapplicable to high-performance filters. In addition, the antibacterial agent adheres to the surface of a filter medium nonuniformly and additional drying and purification processes are necessary.

Besides, the existing antimicrobial filter has the problem that microbe capture ability decreases with time.

RELATED LITERATURES

Patent Literature (Patent document 1) Korean Patent Publication No. 2009-4611

SUMMARY

The present disclosure is directed to providing an antimicrobial filter medium with improved antimicrobial property and microbe capture ability wherein gaseous antimicrobial nanoparticles are uniformly coated onto the filter medium and conductive members are attached on both sides of the filter medium, and an apparatus and a method for fabricating the same.

In an aspect, the present disclosure provides an antimicrobial filter medium wherein a high electric voltage generator is connected to a conductive member on one side of the antimicrobial filter medium, a conductive member on the other side of the antimicrobial filter medium is grounded, and an electric field may be applied between the conductive members by supply of electric power from the high electric voltage generator.

In another aspect, the present disclosure provides an apparatus for fabricating an antimicrobial filter medium, comprising: an antimicrobial droplet generation unit generating antimicrobial droplets by hydraulic pressure spraying an antimicrobial solution in which antimicrobial nanoparticles are dispersed; a dehumidifier unit absorbing and removing a solvent component of the antimicrobial droplet; an electric heater generating antimicrobial nanoparticles by removing a solvent component remaining in the antimicrobial nanoparticles discharged from the dehumidifier unit; an antimicrobial nanoparticle coating unit fabricating an antimicrobial filter medium by coating the antimicrobial nanoparticles generated by the electric heater on a filter medium; and a conductive member coating unit coating conductive members on both sides of the antimicrobial filter medium.

The conductive member coating unit may comprise a conductive member supply unit, an attachment support unit and a conveyor, the conveyor transporting the antimicrobial filter medium fabricated by the antimicrobial nanoparticle coating unit, the conductive member supply unit being provided in the form of a roller above and below the conveyor and supplying the conductive members, and the attachment support unit attaching the conductive members on both sides of the antimicrobial filter medium by pressing them.

The width of the conductive member may be smaller than the width of the antimicrobial filter medium. A high electric voltage generator may be connected to a conductive member on one side of the antimicrobial filter medium, a conductive member on the other side of the antimicrobial filter medium may be grounded, and an electric field may be applied between the conductive members by supply of electric power from the high electric voltage generator. The conductive member conductive member may comprise one of a conductive polymer, a conductive metal filter and a conductive membrane having micropores.

The antimicrobial nanoparticle coating unit may comprise an antimicrobial nanoparticle spray means, a filter medium and a carrier gas suction means, the antimicrobial nanoparticle spray means spraying the antimicrobial nanoparticles generated by the electric heater to the filter medium and the carrier gas suction means sucking a carrier gas introduced into the antimicrobial nanoparticle coating unit.

The antimicrobial nanoparticle spray means may comprise an upper duct providing a space in which the antimicrobial nanoparticles supplied from the electric heater and the carrier gas flow, an upper guide vane provided in the upper duct and uniformly distributing gas flow in the upper duct and an upper porous plate provided in the upper duct and discharging the antimicrobial nanoparticles onto the filter medium, and the carrier gas suction means may comprise a lower porous plate sucking the carrier gas supplied from the antimicrobial nanoparticle spray means through pores, a lower duct providing a space for the carrier gas supplied from the antimicrobial nanoparticle spray means, a lower guide vane uniformly distributing gas flow in the lower duct and a ventilator sucking the carrier gas in the lower duct.

The apparatus for fabricating an antimicrobial filter medium may further comprise an ion generation unit generating ions of a particular polarity, the ions generated by the ion generation unit being bound to the antimicrobial nanoparticles discharged from the electric heater so that the antimicrobial nanoparticles are charged with a particular polarity.

The apparatus for fabricating an antimicrobial filter medium may further comprise a filter medium transport unit transporting the filter medium, the filter medium transport unit being connected to a conveyor of the conductive member coating unit and transporting the fabricated antimicrobial filter medium to the conveyor of the conductive member coating unit.

In another aspect, the present disclosure provides a method for fabricating an antimicrobial filter medium, comprising: hydraulic pressure spraying an antimicrobial solution comprising antimicrobial nanoparticles so as to generate antimicrobial droplets; primarily removing a solvent component of the antimicrobial droplets using a dehumidifier so as to prepare antimicrobial nanoparticles; electrically heating the antimicrobial nanoparticles so as to removing the remaining solvent component; coating the antimicrobial nanoparticles with the solvent component removed onto the surface of a filter medium so as to fabricate an antimicrobial filter medium; and attaching conductive members capable of applying an electric field on both sides of the antimicrobial filter medium.

The antimicrobial filter medium according to the present disclosure and the apparatus and method for fabricating the same provide the following advantageous effects.

Antimicrobial property may be improved by uniformly coating antimicrobial nanoparticles on a filter medium via a gas phase process followed by drying. Also, microbe capture ability may be enhanced by applying an electric field between conductive members provided on both sides of the antimicrobial filter medium.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 3 shows the configuration of an antimicrobial filter medium on which a conductive member is attached;

FIG. 4 shows the configuration of an apparatus for testing the properties of an antimicrobial filter medium according to an exemplary embodiment of the present disclosure;

[Detailed Description of Main Elements]

| | |
|---|---|
| 110: carrier gas supply unit | |
| 120: antimicrobial droplet generation unit | |
| 130: dehumidifier unit | 140: electric heater |
| 150: ion generation unit | |
| 200: antimicrobial nanoparticle coating unit | |
| 210: antimicrobial nanoparticle spray means | |
| 220: carrier gas suction means | |
| 230: filter medium | 240: filter medium transport unit |
| 241: conveyor | 300: conductive member coating unit |
| 310: antimicrobial filter medium | 320: conductive member supply unit |
| 321: conductive member | 330: conveyor |
| 340: attachment support unit | 351: high electric voltage generator |
| 352: ground | |

DETAILED DESCRIPTION

In the present disclosure, antimicrobial nanoparticles are prepared via a gas phase process followed by drying and the antimicrobial nanoparticles are uniformly coated onto a filter medium. Then, conductive members are attached on upper and lower sides of the filter medium so that the filtration efficiency of the filter medium may be improved by applying an electric field between the conductive members.

Hereinafter, an antimicrobial filter medium and an apparatus and a method for fabricating the same according to an exemplary embodiment of the present disclosure will be described in detail referring to the attached drawings.

Figure 1:
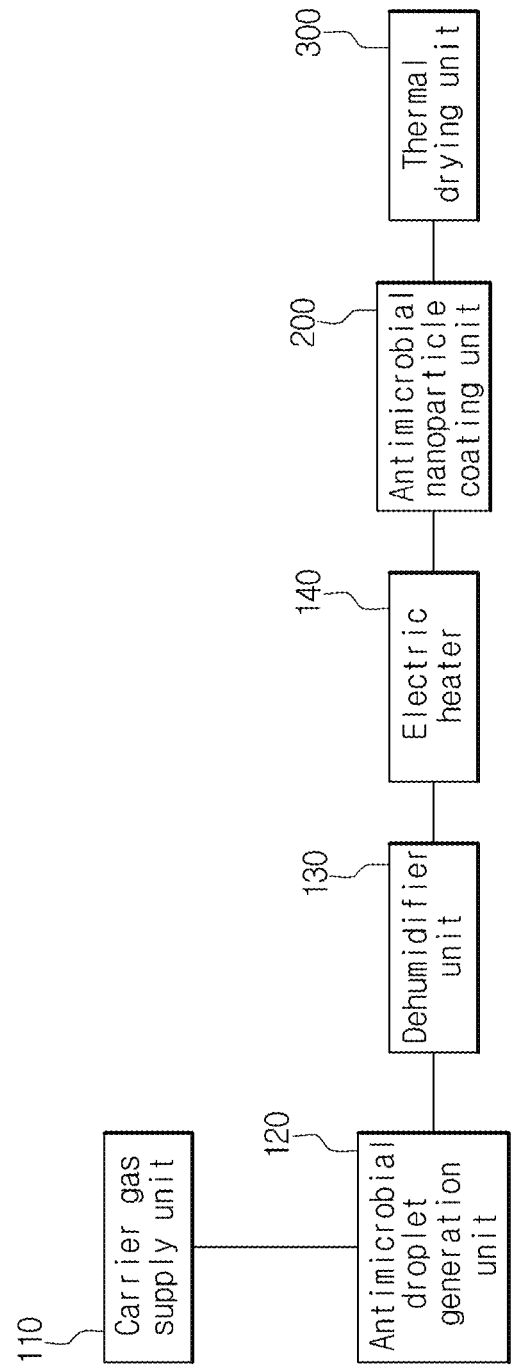
FIG. 1 shows the configuration of an apparatus for fabricating an antimicrobial filter medium according to an exemplary embodiment of the present disclosure.

Referring to FIG. 1, an apparatus for fabricating an antimicrobial filter medium according to an exemplary embodiment of the present disclosure comprises a carrier gas supply unit 110, an antimicrobial droplet generation unit 120, a dehumidifier unit 130, an electric heater 140, an antimicrobial nanoparticle coating unit 200 and a conductive member coating unit 300.

The antimicrobial droplet generation unit 120, the dehumidifier unit 130, the electric heater 140, the antimicrobial nanoparticle coating unit 200 and the conductive member coating unit 300 are configured in an in-line configuration. Accordingly, the fabrication of the antimicrobial filter medium according to the present disclosure is carried out by a series of continuous processes.

The carrier gas supply unit 110 supplies a carrier gas. The carrier gas transports antimicrobial droplets generated by the antimicrobial droplet generation unit 120 and antimicrobial nanoparticles processed by the dehumidifier unit 130 and the electric heater 140. That is to say, the carrier gas is transported through the antimicrobial droplet generation unit 120, the dehumidifier unit 130, the electric heater 140 and the antimicrobial nanoparticle coating unit 200. The carrier gas may be an inert gas such as nitrogen, argon, etc.

The antimicrobial droplet generation unit 120 generates antimicrobial droplets. The antimicrobial droplets are antimicrobial nanoparticles bound to a solvent in the form of droplets. The antimicrobial droplets may be generated by hydraulic pressure spraying. For this, an antimicrobial solution in which the antimicrobial nanoparticles are dissolved or dispersed in a solvent should be prepared in advance, and the antimicrobial droplets may be generated by hydraulic pressure spraying the antimicrobial solution. The solvent may be water or ethanol, and the antimicrobial nanoparticles may be nanoparticles of a natural organic antimicrobial substance such as *Sophora flavescens* extract, *Hosta capitata* extract, chitosan, phytoncide, maple leaf extract, etc. or an inorganic antimicrobial substance such as silver, copper, $TiO_2$, etc. Specifically, the antimicrobial droplets may have a sub-micron size. In addition to the hydraulic pressure spraying method, the antimicrobial droplet may also be generated by a rotary disc method.

The dehumidifier unit 130 serves to primarily remove a solvent component of the antimicrobial droplets. Specifically, it may comprise a chamber having a predetermined volume and a dehumidifier provided in the chamber. The dehumidifier provided in the chamber may be activated carbon, zeolite, etc. The antimicrobial droplets generated by the antimicrobial droplet generation unit 120 are transported to the dehumidifier unit 130 by the carrier gas, and the solvent component of the antimicrobial droplets is primarily removed as the antimicrobial droplets pass through the dehumidifier unit 130, resulting in the discharge of antimicrobial nanoparticles.

The electric heater 140 serves to finally remove the solvent component remaining in the antimicrobial nanoparticles discharged from the dehumidifier unit 130. It may comprise an electrical heating tube having predetermined length and volume and controlled to a predetermined temperature. The solvent component remaining on the surface of the antimicrobial nanoparticles may be removed by passing the antimicrobial nanoparticles through the electrical heating tube. As the solvent component is removed, antimicrobial nanoparticles of sub-micron size may be obtained. Specifically, the electric heater 140 may be controlled in a temperature range of 50-75° C. At temperatures below 50° C., the solvent may not be removed easily. And, at temperatures above 75° C., the natural antimicrobial substance may be degraded.

Figure 2:
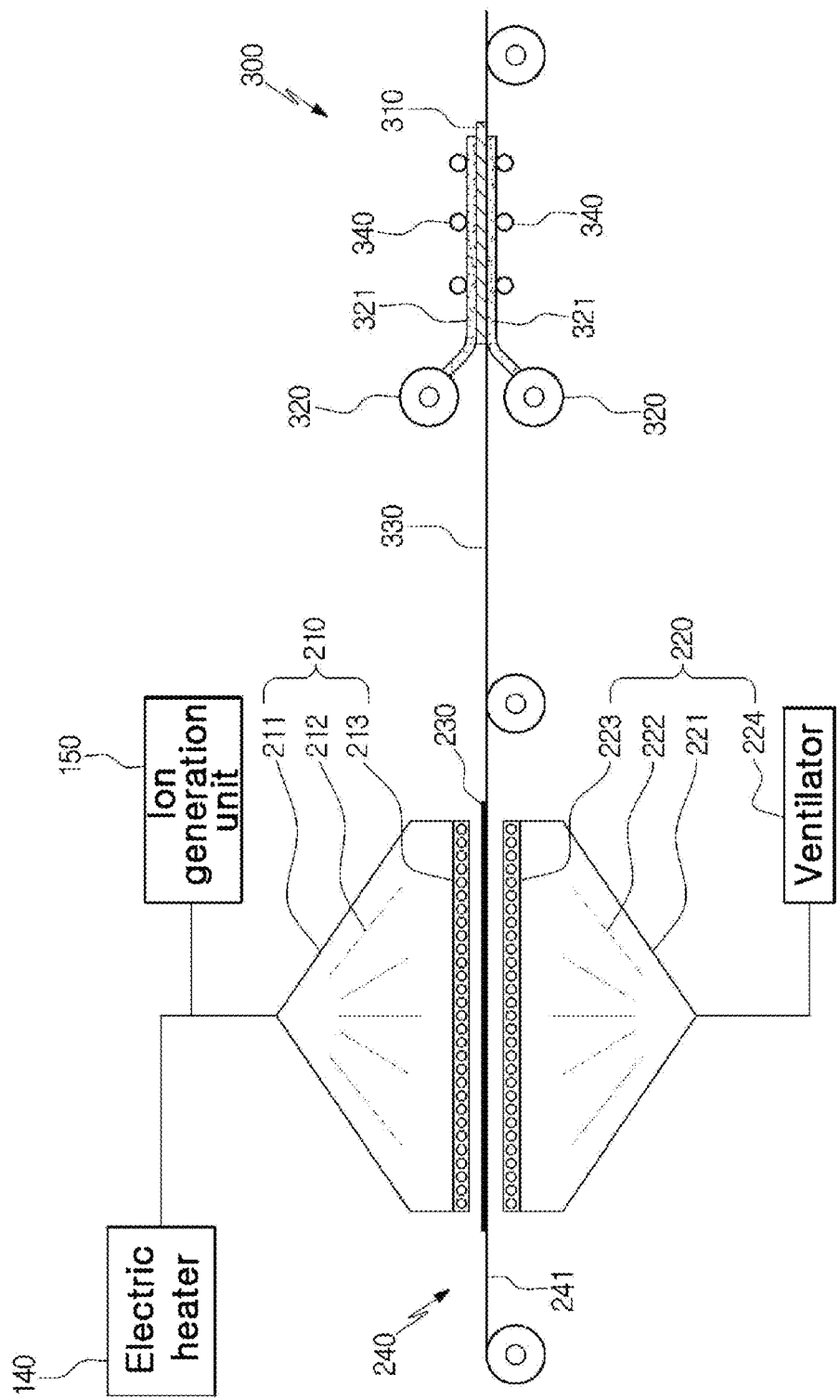
FIG. 2 shows the configuration of an antimicrobial nanoparticle coating unit and a conductive member coating unit according to an exemplary embodiment of the present disclosure.

The antimicrobial nanoparticle coating unit 200 uniformly coats the sub-micron sized antimicrobial nanoparticles generated by the electric heater 140 on the surface of a filter medium 230. Specifically, it comprises an antimicrobial nanoparticle spray means 210, a filter medium 230 and a carrier gas suction means 220, as shown in FIG. 2. The antimicrobial nanoparticle spray means 210 uniformly sprays the antimicrobial nanoparticles onto the filter medium 230, the carrier gas suction means 220 sucks the carrier gas flowing in the antimicrobial nanoparticle coating unit 200, and the filter medium 230 is provided between the antimicrobial nanoparticle spray means 210 and the carrier gas suction means 220.

The antimicrobial nanoparticle spray means 210 comprises an upper duct 211, an upper guide vane 212 and an upper porous plate 213. The upper duct 211 provides a space in which the antimicrobial nanoparticles supplied from the electric heater 140 and the carrier gas flow, the upper guide vane 212 is provided in the upper duct 211 and uniformly distributes gas flow in the upper duct 211, and the upper porous plate 213 allows the antimicrobial nanoparticles in the upper duct 211 to be discharged. The antimicrobial nanoparticles diffuse through the pores of the upper porous plate 213 and are bound onto the surface of the filter medium 230.

The carrier gas suction means 220 comprises a lower porous plate 223, a lower guide vane 222, a lower duct 221 and a ventilator 224. The lower porous plate 223 uniformly sucks the carrier gas supplied from the antimicrobial nanoparticle spray means 210 through a plurality of pores, the lower duct 221 provides a space for the carrier gas supplied from the antimicrobial nanoparticle spray means 210, the lower guide vane 222 uniformly distributes gas flow in the lower duct 221, and the ventilator 224 finally sucks the carrier gas in the lower duct 221. The ventilator 224 may be controlled such that the face velocity of the carrier gas is 10 cm/s or lower.

As described above, the filter medium 230 is provided between the antimicrobial nanoparticle spray means 210 and the carrier gas suction means 220. In addition, a filter medium transport unit 240 is further provided. The filter medium 230 may comprise a fibrous fabric. The filter medium transport unit 240 is configured as a conveyor 241 and serves to transport the filter medium 230. The conveyor 241 of the filter medium transport unit is formed integrally with a conveyor 330 of the conductive member coating unit 300, as will be described later. The filter medium 230 is provided on the filter medium transport unit 240, such that, after the antimicrobial nanoparticles are sprayed onto the filter medium 230 by the antimicrobial nanoparticle spray means 210 and thus bound to the filter medium 230, the filter medium 230 with the antimicrobial nanoparticles bound thereto may be transported by the filter medium transport unit 240. The fibrous fabric may be electrically charged by ions of a particular polarity.

An ion generation unit 150 may be further provided in front of the antimicrobial nanoparticle coating unit 200. The ion generation unit 150 is provided between the electric heater 140 and the antimicrobial nanoparticle coating unit 200 and serves to generate ions of a particular polarity. The ions of a particular polarity generated by the ion generation unit 150 are attached onto the surface of the antimicrobial nanoparticles discharged from the electric heater 140, thus electrically charging the antimicrobial nanoparticles. The electrically charged antimicrobial nanoparticles are supplied to the antimicrobial nanoparticle spray means 210.

When the ions of a particular polarity are generated using the ion generation unit 150 and the antimicrobial nanoparticles are supplied to the antimicrobial nanoparticle spray means 210 after being electrically charged as described above, the filter medium 230 provided between the antimicrobial nanoparticle spray means 210 and the carrier gas suction means 220 may be an electrostatic filter medium 230 or a filter medium 230 electrically charged with a particular polarity. When the filter medium 230 is electrically charged, it has a polarity opposite to that of the electrically charged antimicrobial nanoparticles. Owing to the electrostatic attraction between the electrically charged filter medium 230 and the electrically charged antimicrobial nanoparticles, the antimicrobial nanoparticles may be easily attached and bound to the surface of the filter medium 230.

An antimicrobial filter medium 310 fabricated by the antimicrobial nanoparticle coating unit 200 is transported to the conductive member coating unit 300. The conductive member coating unit 300 serves to coat conductive members 321 on both sides of the antimicrobial filter medium.

The conductive member coating unit 300 comprises a conductive member supply unit 320, an attachment support unit 340 and a conveyor 330. The conveyor 330 is formed integrally with the conveyor 241 of the antimicrobial nanoparticle coating unit 200 and serves to transport the antimicrobial filter medium 310 fabricated by the antimicrobial nanoparticle coating unit 200. The conductive member supply unit 320 is provided in the form of a roller above and below the conveyor 330 and serves to supply the conductive members 321. The attachment support unit 340 serves to attach the conductive members 321 on both sides of the antimicrobial filter medium 310 by pressing the conductive members 321. The width of the conductive member 321 is smaller than the width of the antimicrobial filter medium 310 and, thus, the conductive members 321 are attached to the surface of the antimicrobial filter medium 310 at only part of the entire area (see FIG. 3). Accordingly, by cutting open a portion of the conveyor 330 and providing the attachment support unit 340 along the open portion of the conveyor 330 while transporting the conductive members 321 along the open portion of the conveyor 330, the conductive members 321 may be easily attached on both sides of the antimicrobial filter medium 310 which is transported by the conveyor 330.

The reason why the conductive members 321 are attached on both sides of the antimicrobial filter medium 310 is as follows. Airborne microorganisms are usually electrically charged. In general, the airborne microorganisms are known to be negatively (−) charged. Since the microorganisms are electrically charged, when an electric field is applied between the conductive members 321 on both sides of the antimicrobial filter medium 310 (e.g., when the upper conductive member is positively (+) charged and the lower conductive member is negatively (−) charged), the airborne microorganisms are transported to the antimicrobial filter medium 310, leading to improved microbe capture ability of the antimicrobial filter medium 310. For application of the electric field, a high electric voltage generator 351 is connected to a conductive member 321 provided on one side of the antimicrobial filter medium 310 and a conductive member 321 provided on the other side of the antimicrobial filter medium 310 is connected to a ground 352 (see FIG. 4).

The conductive member 321 may comprise a conductive polymer, a conductive metal filter and a conductive membrane having micropores, or the like. For easier attachment to the antimicrobial filter medium 310, a binder may be coated in advance on the conductive member 321.

An apparatus and a method for fabricating an antimicrobial filter medium according to an exemplary embodiment of the present disclosure were described above. Hereinafter, the properties of the antimicrobial filter medium fabricated according to an exemplary embodiment of the present disclosure will be described.

FIG. 4 shows the configuration of an apparatus for testing the properties of the antimicrobial filter medium of the present disclosure. A mixture solution containing *Staphylococcus epidermidis* was sprayed into the air, passed through a diffusion drying apparatus to remove moisture around the microorganisms (*Staphylococcus epidermidis*) and then passed through the antimicrobial filter medium according to the present disclosure. A high electric voltage generator was connected to a conductive member on one side of the antimicrobial filter medium, a conductive member on the other side of the antimicrobial filter medium was grounded, and an electric field was applied between the conductive members by supply of electric power from the high electric voltage generator.

Figure 5:
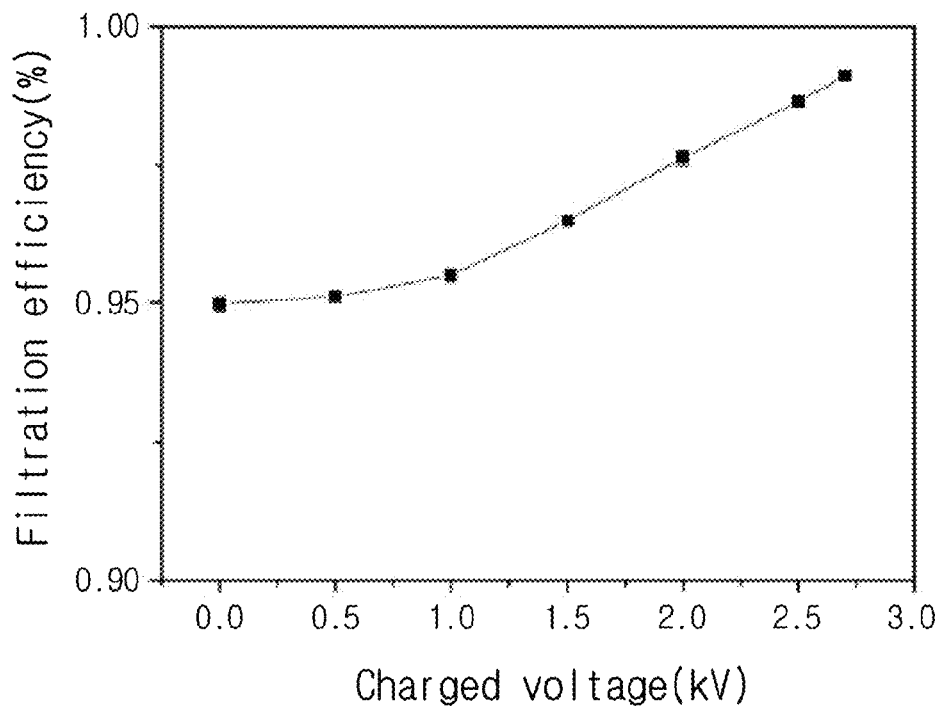
FIG. 5 shows the filtration efficiency of an antimicrobial filter medium depending on the strength of electric field.

FIG. 5 shows the filtration efficiency of the antimicrobial filter medium depending on the strength of electric field. Referring to FIG. 5, it can be seen that the filtration efficiency of the antimicrobial filter medium is improved as the strength of electric field is increased. The filtration efficiency of the antimicrobial filter medium is defined as the ratio of the microorganism particle concentration of the air before and after passing through the antimicrobial filter medium.

Figure 6:
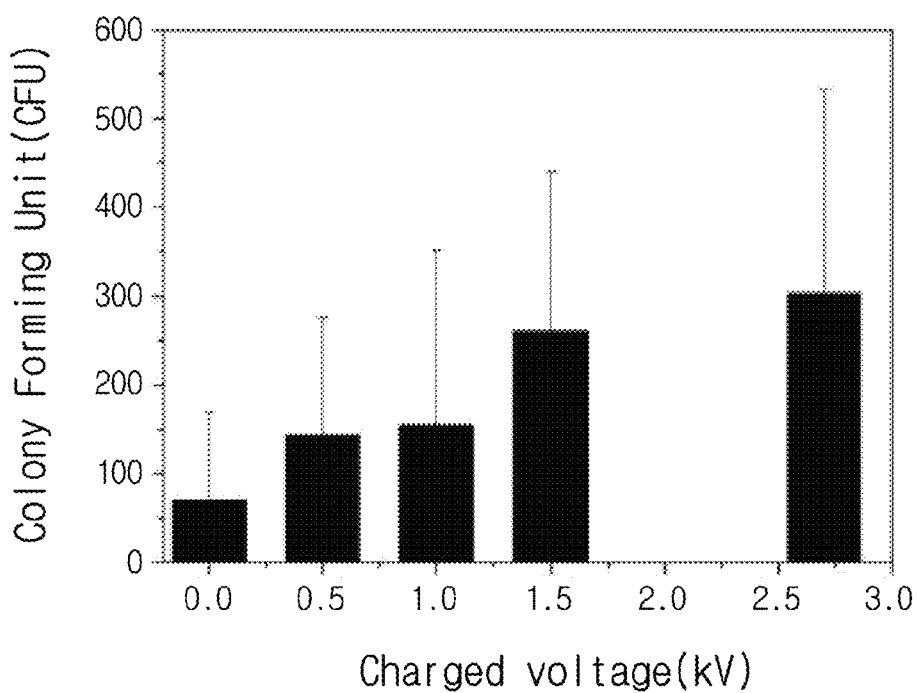
FIG. 6 shows the microbe capture efficiency of an antimicrobial filter medium depending on the strength of electric field.

FIG. 6 shows the microbe capture efficiency of the antimicrobial filter medium depending on the strength of electric field. Referring to FIG. 6, it can be seen that the concentration of the microorganisms captured by the antimicrobial filter medium increases as the strength of electric field is increased. The concentration of the microorganisms was determined by isolating the microorganisms from the antimicrobial filter medium and growing in a culture medium and then measuring the colony forming unit of the microorganisms.

Figure 7:
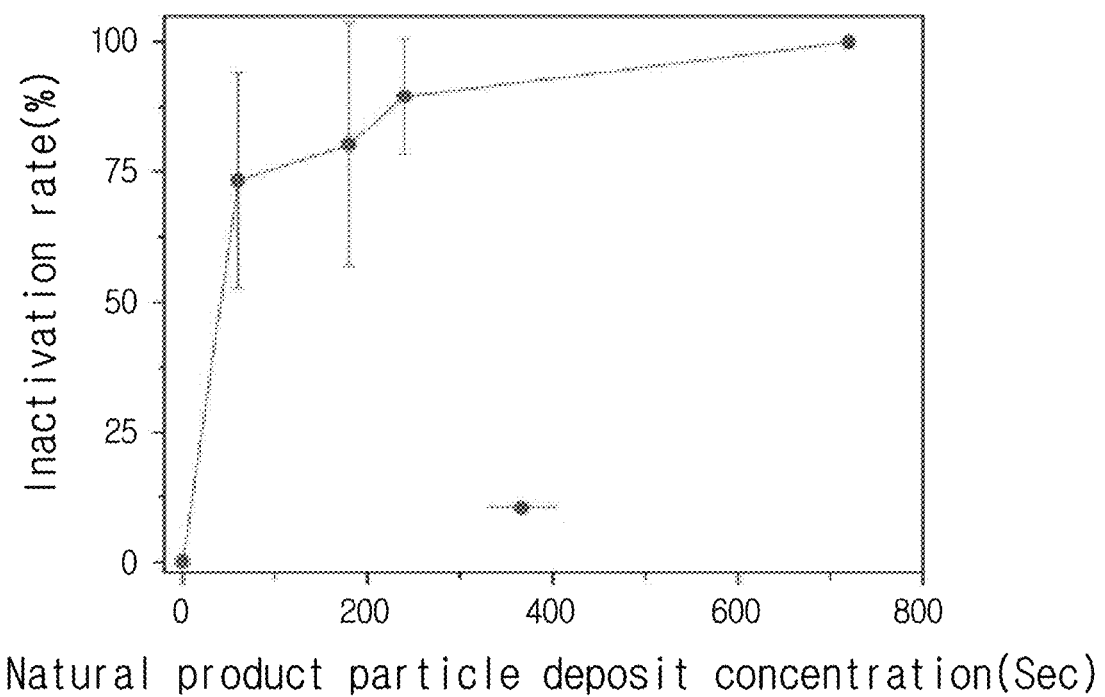
FIG. 7 shows the antimicrobial performance of an antimicrobial filter medium depending on the amount of antimicrobial nanoparticles coated on the antimicrobial filter medium.

FIG. 7 shows the antimicrobial performance of the antimicrobial filter medium depending on the amount of antimicrobial nanoparticles coated on the antimicrobial filter medium. It can be seen that the antimicrobial performance of the antimicrobial filter medium is improved as the strength of electric field is increased.

While the exemplary embodiments have been shown and described, it will be understood by those skilled in the art that various changes in form and details may be made thereto without departing from the spirit and scope of the present disclosure as defined by the appended claims.

What is claimed is:

1. An apparatus for fabricating an antimicrobial filter medium, comprising:
   an antimicrobial droplet generation unit configured to generate antimicrobial droplets by hydraulic pressure spraying an antimicrobial solution in which antimicrobial nanoparticles are dispersed;
   a dehumidifier unit configured to absorb and remove a solvent component of the antimicrobial droplet;
   an electric heater configured to generate antimicrobial nanoparticles by removing a solvent component remaining in the antimicrobial nanoparticles discharged from the dehumidifier unit:
   an antimicrobial nanoparticle coating unit configured to fabricate an antimicrobial filter medium by coating the antimicrobial nanoparticles generated by the electric heater on a filter medium; and
   a conductive member coating unit configured to coat conductive members on both sides of the antimicrobial filter medium,
   wherein the conductive member coating unit comprises a conductive member supply unit, an attachment support unit and a conveyor, and
   wherein the conveyor is configured to transport the antimicrobial filter medium fabricated by the antimicrobial nanoparticle coating unit, the conductive member supply unit comprises a roller above and below the conveyor and is configured to supply the conductive members, and the attachment support unit is configured to attach the conductive members on both sides of the antimicrobial filter medium by pressing them.

2. The apparatus for fabricating an antimicrobial filter medium according to claim 1, wherein the width of the conductive member is smaller than the width of the antimicrobial filter medium.

3. The apparatus for fabricating an antimicrobial filter medium according to claim 1, wherein a high electric voltage generator is connected to a conductive member on one side of the antimicrobial filter medium, a conductive member on the other side of the antimicrobial filter medium is grounded, and wherein the high electric voltage generator is configured to supply electric power in order to apply an electric field between the conductive members.

4. The apparatus for fabricating an antimicrobial filter medium according to claim 1, wherein the conductive member comprises one of a conductive polymer, a conductive metal filter and a conductive membrane having micropores.

5. The apparatus for fabricating an antimicrobial filter medium according to claim 1, wherein the antimicrobial nanoparticle coating unit comprises an antimicrobial nanoparticle spray means, a filter medium and a carrier gas suction means, the antimicrobial nanoparticle spray means configured to spray the antimicrobial nanoparticles generated by the electric heater to the filter medium and the carrier gas suction means configured to suck a carrier gas introduced into the antimicrobial nanoparticle coating unit.

6. The apparatus for fabricating an antimicrobial filter medium according to claim 5,
wherein the antimicrobial nanoparticle spray means comprises an upper duct providing a space in which the antimicrobial nanoparticles supplied from the electric heater and the carrier gas flow, and an upper guide vane provided in the upper duct and configured to uniformly distribute gas flow in the upper duct and an upper porous plate provided in the upper duct and configured to discharge the antimicrobial nanoparticles onto the filter medium, and
wherein the carrier gas suction means comprises a lower porous plate configured to suck the carrier gas supplied from the antimicrobial nanoparticle spray means through pores, a lower duct configured to provide a space for the carrier gas supplied from the antimicrobial nanoparticle spray means, and a lower guide vane configured to uniformly distribute gas flow in the lower duct and a ventilator sucking the carrier gas in the lower duct.

7. The apparatus for fabricating an antimicrobial filter medium according to claim 1, which further comprises an ion generation unit configured to generate ions of a particular polarity, wherein the ions generated by the ion generation unit are bound to the antimicrobial nanoparticles discharged from the electric heater so that the antimicrobial nanoparticles are charged with a particular polarity.

8. The apparatus for fabricating an antimicrobial filter medium according to claim 5, which further comprises a filter medium transport unit configured to transport the filter medium, connected to a conveyor of the conductive member coating unit, and configured to transport the fabricated antimicrobial filter medium to the conveyor of the conductive member coating unit.

9. An apparatus for fabricating an antimicrobial filter medium, comprising:
an antimicrobial droplet generation unit configured to generate antimicrobial droplets by hydraulic pressure spraying an antimicrobial solution in which antimicrobial nanoparticles are dispersed;
a dehumidifier unit configured to absorb and remove a solvent component of the antimicrobial droplet;
an electric heater configured to generate antimicrobial nanoparticles by removing a solvent component remaining in the antimicrobial nanoparticles discharged from the dehumidifier unit:
an antimicrobial nanoparticle coating unit configured to fabricate an antimicrobial filter medium by coating the antimicrobial nanoparticles generated by the electric heater on a filter medium; and
a conductive member coating unit configured to coat conductive members on both sides of the antimicrobial filter medium,
wherein the conductive member coating unit comprises a conductive member supply unit, an attachment support unit and a conveyor, and
wherein the conveyor is configured to transport the antimicrobial filter medium fabricated by the antimicrobial nanoparticle coating unit, the conductive member supply unit comprises a roller above and below the conveyor and is configured to supply the conductive members, and the attachment support unit is configured to attach the conductive members on both sides of the antimicrobial filter medium by pressing them,
wherein an antimicrobial filter medium is fabricated by the apparatus, and
wherein a high electric voltage generator is connected to a conductive member on one side of the antimicrobial filter medium, a conductive member on the other side of the antimicrobial filter medium is grounded, and an electric field may be applied between the conductive members by supply of electric power from the high electric voltage generator.

* * * * *